United States Patent
Sano et al.

(10) Patent No.: US 6,414,159 B2
(45) Date of Patent: Jul. 2, 2002

(54) METHOD FOR PREPARATION OF A QUATERNARY AMMONIUM SALT

(75) Inventors: Kimihiko Sano; Yoji Urano; Takuhiro Kimura; Atsunori Sano, all of Saitama (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/779,743

(22) Filed: Feb. 9, 2001

(30) Foreign Application Priority Data

Feb. 14, 2000 (JP) ........................ 2000-034564

(51) Int. Cl.⁷ ................... C07D 213/20; C07D 233/58
(52) U.S. Cl. .................... 546/347; 548/343.1
(58) Field of Search .................. 546/347; 548/343.1

(56) References Cited

FOREIGN PATENT DOCUMENTS

| GB | 379396 | 9/1932 |
|----|--------|--------|
| WO | WO 98/09668 | 3/1998 |

OTHER PUBLICATIONS

N. N. Borisova et al.; "Synthesis of salts of quaternary ammonium bases having antibacterial activity," Chemical Abstracts, vol. 69, No. 1, Jul. 1, 1998, pp. 2838–2840.

P. Bonhote et al.; "Hydrophobic, Highly Conductive Ambient–Temperature Molten Salts," Inorganic Chemistry, US, American Chemical Society, Easton, vol. 35, No. 5, 1996, pp. 1168–1178.
Von P. Karrer et al.; Helv. Chim.Acta 21, pp. 223–236, 1938.
Knight et al.; J. Chem. Soc., pp. 682–683, 1938. Discussed in the specification.
Shelton et al., J. Am. Chem.Soc. 68, pp. 757–759, 1946. Discussed in the specification.
Barni et al.; J. Heterocycl. Chem.23(1)pp. 209–221, 1986. Discussed in the specification.
Bonhôte et al.; Inorg.Chem.35(5)pp. 1168–1178, 1996. Discussed in the specification.

*Primary Examiner*—Patricia L. Morris
(74) *Attorney, Agent, or Firm*—Armstrong, Westerman, Hattori, LLP

(57) ABSTRACT

The present invention provides a method for preparation of a quaternary ammonium salt comprising reacting an alkyl halide with 2 equimolar amount or more per the alkyl halide of a pyridine compound or an N-lower alkyl imidazole at 120° C. to 350° C., and a method for the continuous production of a quaternary ammonium salt comprises introducing continuously an alkyl halide and 2 equimolar amount or more per the alkyl halide of a pyridine compound or an N-lower alkyl imidazole into a pipe reactor from the one end thereof under heating at 120 to 350° C. to pass through the pipe reactor wherein a reaction is allowed to take place, and taking out continuously the resulting quaternary ammonium salt from the other end of the reactor.

14 Claims, 1 Drawing Sheet

METHOD FOR PREPARATION OF A QUATERNARY AMMONIUM SALT

BACKGROUND OF INVENTION

The present invention relates to a method for preparation of a quaternary ammonium salt at high yield in a short reaction time.

Quaternary ammonium salts have been a remarkably important compound as starting materials for medicines and quasi-drugs and cosmetics, phase-transfer catalysts, ionized solvents, etc. Among the salts, quaternary pyridinium salts have recently be noticed mainly as an antibacterial agent and have been thought to increase its demand in future. However, it has been difficult to produce those compounds in an industrial scale at high efficacy in a short period of time. For instance, there has been disclosed a method comprising reacting dodecyl chloride with pyridine at 100° C. for 24 hours in J. Chem. Soc., 682(1938) and a method comprising reacting an alkyl halide with 10 to 30% excess amount of pyridine at 60 to 130° C. for 8 to 16 hours in J. Am. Chem. Soc. 68, 757–759(1946). However, in the former method, the reaction time is long and further yield of the object compound, a quaternary pyridinium salt, is such low as 1.7%, and in the latter method, the yield is considerably such high as 95% but the reaction time is remarkably long such as 8 to 16 hours, and therefore both methods are not satisfactory as a method for production of a quaternary ammonium salt in an industrial scale.

There has been also disclosed a method comprising reacting picoline, the methyl-substituted pyridine, with an alkyl halide under refluxing for 12 hours to obtain a quaternary picolinium salt in J. Heterocycl. Chem. 23(1) 209–221(1986). However, the reaction time is so long, and thus this method is not satisfactory as a method for production of a quaternary picolinium salt in an industrial scale.

On the other side, a quaternary imidazolinium salt as well as a quaternary pyridinium salt have been thought to increase its demand in future, and there has been disclosed a method comprising reacting an alkyl halide with methyl imidazole under refluxing in an organic solvent to obtain a quaternary imidazolinium salt in Inorg. Chem. 35(5) 1168–1178(1996). However, this method can not be easily conducted because of using a organic solvent and the yield is also low, and therefore this method is not satisfactory as a method for production of a quaternary imidazolinium salt in an industrial scale.

Furthermore, since a preparation for a quaternary ammonium salt as mentioned above have been conducted by batch process, its productivity is low and therefore those methods are not suitable for production in an industrial scale.

SUMMARY OF INVENTION

The present invention has been accomplished under such circumstances as above and its object is to provide a method for preparation of a quaternary ammonium salt by reacting a pyridine compound or an N-lower alkyl imidazole (hereinafter the pyridine compound and the N-lower alkyl imidazole are, sometimes, inclusively abbreviated as heterocyclic compound of the present invention) with an alkyl halide in an industrial scale at high efficiency in a short reaction time.

The present invention relates to a method for preparation of a quaternary ammonium salt comprising reacting an alkyl halide with 2 equimolar amount or more per the alkyl halide of a pyridine compound or an N-lower alkyl imidazole at 120° C. to 350° C.

Further, the present invention relates to a method for the continuous production of a quaternary ammonium salt comprises introducing continuously an alkyl halide and 2 equimolar amount or more per the alkyl halide of a heterocyclic compound of the present invention into a pipe reactor from the one end thereof under heating at 120 to 350° C. to pass through the pipe reactor wherein a reaction is allowed to take place, and taking out continuously the resulting quaternary ammonium salt from the other end of the reactor.

Namely, the present inventors have extensively conducted study in order to fulfill the above object to arrive at the finding that a quaternary ammonium salt can be produced effectively in a short reaction time by reacting an alkyl halide with 2 equimolar amount or more per the alkyl halide of a pyridine compound or an N-lower alkyl imidazole at 120° C. to 350° C., and the present invention has been completed on the basis of this finding.

PREFERRED EMBODIMENTS OF INVENTION

Figure 1:
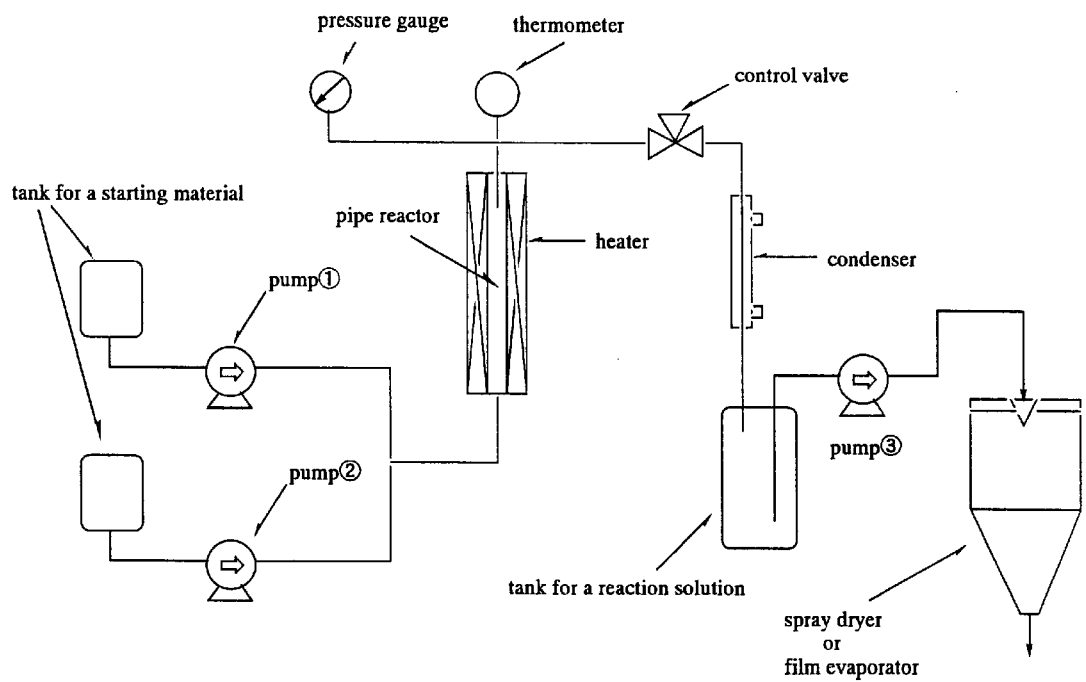
FIG. 1 shows the continuous reaction plant used in Example 4 and 5.

The N-lower alkyl imidazole includes one in which a hydrogen atom binding to a nitrogen atom is substituted by a lower alkyl group having 1 to 4 carbon atoms such as a methyl group, an ethyl group, an n-propyl group, an iso-propyl group, an n-butyl group, an iso-butyl group, a tert-butyl group, a sec-butyl group etc., and is specifically exemplified by N-methylimidazole, N-ethylimidazole, N-n-propylimidazole, N-isopropylimidazole, N-n-butylimidazole, N-iso-butylimidazole, N-tert-butylimidazole, N-sec-butylimidazole etc., among which N-methylimidazole is preferable.

The pyridine compound of the present invention includes pyridine or a pyridine derivative whose 1 to 3 hydrogen atoms are substituted by a lower alkyl group having 1 to 4 carbon atoms mentioned above, which is specifically exemplified by picoline, dimethyl pyridine, trimethyl pyridine, ethyl pyridine, propyl pyridine, butyl pyridine etc, among which pyridine and picoline are preferable.

The alkyl halide of the present invention includes one shown by the following general formula [1]

$$R_1 - Y \qquad [1]$$

(wherein $R_1$ is an alkyl group and Y is a halogen atom).

The alkyl group shown by $R_1$ in the general formula [1] may be straight chained or branched and includes one having generally 1 to 30 carbon atoms, preferably 1 to 24 carbon atoms, more preferably 3 to 24 carbon atoms, which is specifically exemplified by a methyl group, an ethyl group, an n-propyl group, an iso-propyl group, an n-butyl group, an iso-butyl group, a sec-butyl group, a tert-butyl group, an n-pentyl group, an isopentyl group, a sec-pentyl group, a tert-pentyl group, a neopentyl group, an n-hexyl group, an isohexyl group, a 3-methylpentyl group, a 2-methylpentyl group, a 1-methylpentyl group, a 1-ethylbutyl group, a 2-ethylbutyl group, a 1,2-dimethylbutyl group, a 2,3-dimethylbutyl group, an n-heptyl group, an n-octyl group, an n-nonyl group, an n-decyl group, an n-undecyl group, an n-dodecyl group, an n-tridecyl group, an n-tetradecyl group, an n-pentadecyl group, an n-cetyl group, an n-heptadecyl group, an n-octadecyl group, an n-nonadecyl group, an n-icosyl group, an n-henicosyl group, an n-docosyl group, an n-tricosyl group, an n-tetracosyl group, an n-pentacosyl group, an n-hexacosyl group, an n-octacosyl group, an n-nonacosyl group, an n-triacontyl group, etc.

The halogen atom shown by Y includes a fluorine atom, a chlorine atom, an iodine atom, a bromine atom, etc.

The quaternary ammonium salt of the present invention can be shown by the following general formula [2] or [3]

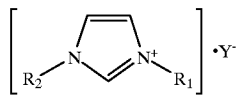

[2]

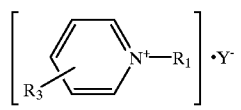

[3]

(wherein $R_2$ is a lower alkyl group having 1 to 4 carbon atoms mentioned above, $R_3$ is a hydrogen atom or one to three lower alkyl groups having 1 to 4 carbon atoms mentioned above and $R_1$ and Y have the same meaning as above).

Specific examples of the quaternary ammonium salts obtained by reacting an alkyl halide with an N-lower alkyl imidazole are as follows.

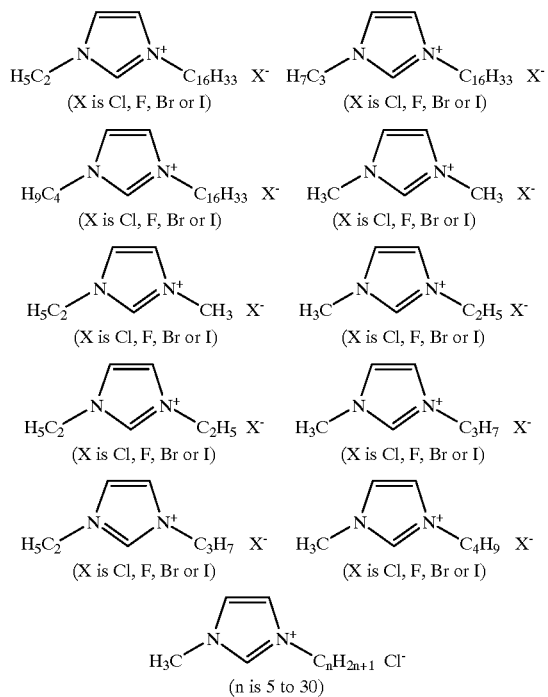

Specific examples of the quaternary ammonium salts obtained by reacting an alkyl halide with a pyridine compound are as follows including those of which 1 to 3 hydrogen atoms are substituted by a lower alkyl group having 1 to 4 carbon atoms.

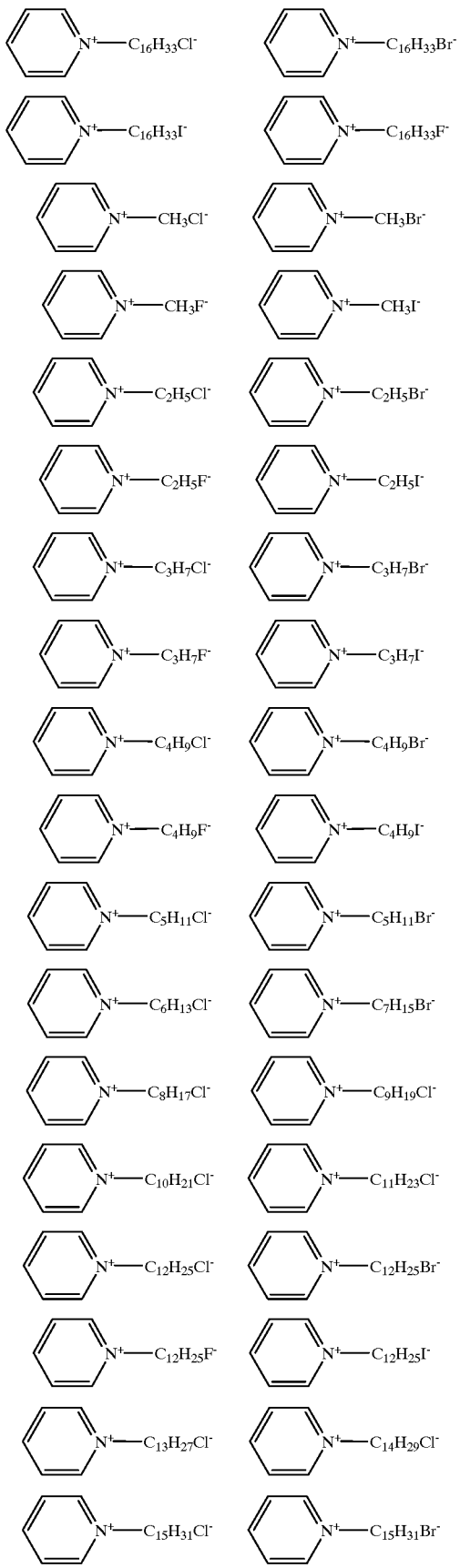

-continued

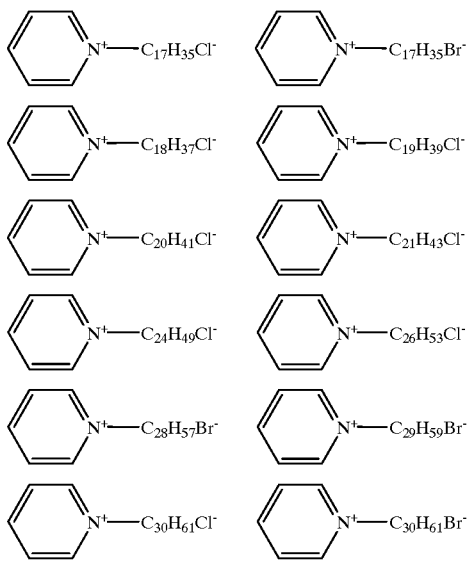

The preparation of the quaternary ammonium salt by the present invention is realized, for instance, by reacting the alkyl halide with 2 equimolar amount or more per the alkyl halide of the heterocyclic compound of the present invention in an airtight container such as autoclave at 120° C. to 350° C., among which the continuous preparation of a quaternary ammonium salt using a pipe reactor is preferable, and may be conducted concretely by a method mentioned below.

Namely, the alkyl halide and the heterocyclic compound of the present invention are charged into a pipe reactor from the one end thereof continuously, for instance, with a pump at the introduction speed mentioned below and those compounds are passed through the pipe reactor which is kept at the desired temperature, wherein the reaction is allowed to take place continuously, and then the reaction product produced in the reactor is taken out from the other end of the reactor continuously. On conducting this method, the pressure in the pipe reactor may be controlled by installing a control valve equipped on the end of the pipe reactor. Even when the pressure is increased too high, the reaction efficacy is not increased, and thus the pressure may be adjusted to generally 1 to 100 kg/cm², preferably 2 to 20 kg/cm², more preferably 2 to 10 kg/cm². The quaternary ammonium salt taken from the pipe reactor may be subjected to the after-treatment which has so far been conducted generally in this kind of technical field, such as crystallization with a spray dryer or a film evaporator.

The pipe reactor of the present invention includes those having two openings at the both ends, which can be made into sealed condition by closing the openings and is durable ever under high temperature and high pressure, and among them, preferable ones are those wherein heat is conducted up to the inner part by heating from the outer side.

A typical example of the pipe reactor is one made of stainless steal of which shape can be kept without deformation under heating up to about 500° C. under pressure up to about 100 kg/cm².

The introduction speed of the compounds to be charged into the reactor is adjusted on the basis of the inner volume of the reactor and the time required for the objection reaction, and it is preferably in proportion to the volume of the pipe reactor, namely the introduction speed is adjusted to twice when the volume of the pipe reactor is twice, for instance more concretely, the introduction speed of those compounds is generally shown by the following equations, $$(p/q) \leq r \leq [p/(q \times 10)]$$

(wherein, p(ml) is the volume of the reactor, q(min) is the time required for the object reaction and r(ml/min) is the introduction speed of the compounds.) preferably, $$(p/q) \leq r \leq [p/(q \times 2)]$$

particular preferably, $$p/q = r$$

On setting forth the introduction speed of the compounds by using the above equations, it is preferable that the volume of the pipe reactor is adjusted according to the required amount of a quaternary ammonium salt etc. and the time required for the reaction is set forth according to the combination of the kinds of starting materials (as mentioned below, it is generally 5 minutes to 6 hours), and then the introduction speed is calculated by the equations using thus determined values. The introduction speed means the total amount of the alkyl halide and the heterocyclic compound of the present invention to be introduced per unit of time, and a ratio of these two compounds are such one as 2 equimolar amount or more per the alkyl halide of the heterocyclic compound of the present invention per the alkyl halide. The alkyl halide is mixed with 2 equimolar amount or more per the alkyl halide of the heterocyclic compound of the present invention, and then the mixture may be introduced into the pipe reactor at the introduction speed adjusted as mentioned above. More particularly, for instance, when the volume of the pipe reactor is set forth as 200 ml and the time required for the reaction is set forth as 15 minutes, then the introduction speed is calculated as 200 ml÷15 min≈13.3 ml/min, and on the basis of this value it can be determined generally as 1.3 to 13.3 ml/min, preferably as 6.7 to 13.3 mil/min, still preferably as 13.3 ml/min.

An amount of the heterocyclic compound of the present invention to be used is generally 2 equimolar amount or more per the alkyl halide, whereupon the desired reaction can be completed by adjusting the reaction temperature of 120° C. to 350° C., and preferably the amount is 2 to 20 equimolar amount, more preferably it is 3 to 10 equimolar amount.

When an amount of the heterocyclic compound of the present invention to be used is a theoretical amount or a slightly excess amount to the alkyl halide, the reaction is not completed even after a long reaction time.

The reaction temperature is generally 120° C. to 350° C., preferably 140 to 300° C., more preferably 150 to 250° C.

The preparation of the present invention may be conducted under streams of an inert gas such as helium gas, nitrogen gas and argon gas and, in this case, the reaction temperature may be increased by elevating pressure of the inert gas in the reaction system. Even when the pressure is increased too high, the reaction efficacy is not increased, and thus the pressure may be adjusted to generally 1 to 100 kg/cm², preferably 2 to 20 kg/cm², more preferably 2 to 10 kg/cm².

The reaction time is generally 5 minutes to 6 hours, preferably 5 minutes to 2 hours, more preferably 5 to 30 minutes.

The after-treatment of the present invention may be conducted according to the general method of after treatment in this kind of technical field.

By using the method of the present invention, a quaternary ammonium salt can be obtained effectively and easily in a short reaction time even without setting severe reaction conditions.

The quaternary ammonium salt obtained by the method of the present invention is useful as starting materials for medicines, quasi-drugs, cosmetics, etc., phase-transfer catalysts, ionized solvents, antibacterial agents, etc.

In the following, the present invention is explained in details with reference to Examples, and the present invention is not limited thereto by any means.

EXAMPLE

Example 1

Nitrogen gas was introduced in an autoclave charged with 115.1 g (0.44 mole) of n-cetyl chloride and 146.6 g (1.85 mole) of pyridine to adjust the pressure in the autoclave to 2 kg/cm$^2$, followed by agitation at 180° C. for 15 minutes to allow a reaction to take place.

After the reaction, the reaction solution was dried under reduced pressure to give powdery crystal.

The reaction solution after the reaction was analyzed by HPLC to confirm the reaction rate to be 100%. To the obtained powdery crystal was added 316 ml of methylethyl ketone, followed by agitation at room temperature, and the resulting crystal was recovered by filtration, washed with methylethyl ketone and dried under reduced pressure to give 142.5 g of powdery crystal (yield 95%). The obtained crystal was determined as cetyl pyridinium chloride by measuring the melting point and $^1$HNMR analysis.

Treatment of the obtained cetyl pyridinium chloride with water easily gave n-cetyl pyridinium chloride monohydrate.

Example 2

The same process as in Example 1 except for agitation at 160° C. for 30 minutes was conducted to give n-cetyl pyridinium chloride. After the reaction, the reaction solution was analyzed by HPLC to confirm the reaction rate to be 100%.

Control Example 1

115.1 Grams (0.44 mole) of n-cetyl chloride and 146.6 g (1.85 mole) of pyridine were subjected to a reaction under refluxing at 96 to 100° C. under nitrogen gas streams. The reaction solution at 15 minutes after the start of the reaction was analyzed by HPLC to find the reaction rate to be 3%.

Control Example 2

Nitrogen gas was introduced into an autoclave charged with 115.1 g (0.44 mole) of n-cetyl chloride and 38.4 g (0.44 mole) of pyridine to adjust the pressure in the autoclave to 2 kg/cm$^2$, followed by agitation at 160° C. for 4 hours to allow a reaction to take place. After the reaction, the reaction solution was analyzed by HPLC to find the reaction rate to be 80%.

Example 3

Nitrogen gas was introduced into an autoclave charged with 40.8 g (0.44 mole) of n-butyl chloride and 146.6 g (1.85 mole) of pyridine to adjust the pressure in the autoclave to 2 kg/cm$^2$, followed by agitation at 180° C. for 15 minutes to allow a reaction to take place. After the reaction, the reaction solution was analyzed by HPLC to find the reaction rate to be 100%.

As clear from comparing Example 1, 2 and 3 on one hand with Control Example 1 and 2 on the other hand, it is found that the reaction rate can be increased and further the reaction time can remarkably be shortened and thus the object quaternary ammonium salt can be obtained effectively by adjusting the amount of pyridine to be used to 2 equimolar amount or more per the alkyl halide and conducting the reaction at 120° C. to 350° C.

Example 4

Using the continuous reaction plant equipped with the pipe reactor of 200 ml as shown in the FIG. 1, n-cetyl chloride was continuously introduced into the pipe reactor at 6.29 ml/min with pump①  and at the same time pyridine was continuously introduced into the pipe reactor at 7.04 mmin with pump② to adjust the inner pressure of the pipe reactor to 5 kg/cm$^2$ and the inner temperature to 180° C.

The reaction solution (261.7 g) taken from the end of condenser was dried under reduced pressure with the spray dryer to obtain 150 g of powdery crystal(yield 100%). Analysis of the reaction solution by HPLC showed the reaction rate to be 100%. After the same treatment of the above obtained powdery crystal as in Example 1 gave 141.0 g of powdery crystal (yield 94%).

Example 5

The same process as in Example 4 except for using a film evaporator in place of a spray dryer was conducted to give n-cetyl pyridinium chloride. After the reaction, the reaction solution was analyzed by HPLC to confirm the reaction rate to be 100%.

As clear from the result of Example 4 and 5, it is found that quaternary pyridinium salt can be produced continuously by using the plant equipped with the pipe reactor as shown in the FIG. 1 at the same high yield and high reaction rate as in Examples 1 to 3.

Example 6

Nitrogen gas was introduced into an autoclave charged with 95.9 g (0.70 mole) of n-butyl bromide and 241.4 g (2.94 mole) of 1-methyl imidazole to adjust the pressure in the autoclave to 2 kg/cm$^2$, followed by agitation at 160° C. for 30 minutes to allow a reaction to take place. After the reaction, the reaction solution was analyzed by NMR to find the reaction rate to be 100%.

Example 7

Nitrogen gas was introduced into an autoclave charged with 182.6 g (0.70 mole) of n-cetyl chloride and 241.4 g (2.94 mole) of 1-methyl imidazole to adjust the pressure in the autoclave to 2 kg/cm$^2$, followed by agitation at 180° C. for 30 minutes to allow a reaction to take place. After the reaction, the reaction solution was analyzed by NMR to find the reaction rate to be 100%.

Example 8

Nitrogen gas was introduced into an autoclave charged with 52.1 g (0.38 mole) of n-butyl bromide and 178.4 g (1.92 mole) of 4-picoline to adjust the pressure in the autoclave to 2 kg/cm$^2$, followed by agitation at 160° C. for 15 minutes to allow a reaction to take place. After the reaction, the reaction solution was analyzed by NMR to find the reaction rate to be 100%.

Example 9

Nitrogen gas was introduced into an autoclave charged with 100.0 g (0.38 mole) of n-cetyl chloride and 178.4 g (1.92 mole) of 4-picoline to adjust the pressure in the autoclave to 2 kg/cm$^2$, followed by agitation at 180° C. for 15 minutes to allow a reaction to take place. After the reaction, the reaction solution was analyzed by NMR to find the reaction rate to be 94%.

As clear from the result of Examples 6 to 9, it is found that a quaternary ammonium salt derived from methyl imidazole or picoline can be produced effectively in a short reaction time just like as the quaternary pryridinium salt.

EFFECT OF INVENTION

The present invention is to provide a method for preparation of a quaternary ammonium salt effectively in a short reaction time by reacting an alkyl halide with a heterocyclic compound of the present invention, and according to the method of the present invention, all of problems found in known methods, namely requirements for severe reaction conditions and complicated reaction process steps and a poor reaction rate and a long reaction time, can be solved. Further, the object quaternary ammonium salt can continuously be produced by conducting the reaction in a pipe reactor of the present invention, and thus the method of the present invention is excellent also from industrial point of view.

What is claimed is:

1. A method for preparation of a quaternary ammonium salt, which comprises reacting an alkyl halide with 2 equimolar amount or more per the alkyl halide of a pyridine compound or an N-lower alkyl imidazole at 120 to 350° C.

2. A method according to claim 1, wherein the reaction temperature is 140 to 300° C.

3. A method according to claim 1, wherein the pyridine compound is pyridine or a pyridine derivative having a lower alkyl group at hydrogen atom(s) of the pyridine ring.

4. A method according to claim 1, wherein the N-lower alkyl imidazole is N-methylimidazole.

5. A method according to claim 1, wherein the alkyl halide is a cetyl halide.

6. A method according to claim 1, wherein the alkyl halide is cetyl chloride and the pyridine compound or an N-lower alkyl imidazole is pyridine.

7. A method for continuous production of a quaternary ammonium salt comprises introducing continuously an alkyl halide and 2 equimolar amount or more per the alkyl halide of a pyridine compound or an N-lower alkyl imidazole into a pipe reactor from the one end thereof under heating at 120 to 350° C. to pass through the reactor wherein a reaction is allowed to take place, and taking out continuously the resulting quaternary ammonium salt from the other end of the reactor.

8. A method according to claim 7, wherein the temperature is 140 to 300° C.

9. A method according to claim 7, wherein the pyridine compound is pyridine or a pyridine derivative having a lower alkyl group at hydrogen atom(s) of the pyridine ring.

10. A method according to claim 7, wherein the N-lower alkyl imidazole is N-methylimidazole.

11. A method according to claim 7, wherein the alkyl halide is a cetyl halide.

12. A method according to claim 7, wherein the alkyl halide is cetyl chloride and the pyridine compound or the N-lower alkyl imidazole is pyridine.

13. A method according to claim 7, wherein an introduction speed of the pyridine compound or the N-lower alkyl imidazole and the alkyl halide and a volume of the reactor are adjusted in such a way that the reaction is completed around the end position of the reactor.

14. A method according to claim 13, wherein the alkyl halide is cetyl chloride and the pyridine compound or the N-lower alkyl imidazole is pyridine.

* * * * *